(12) United States Patent
Savord et al.

(10) Patent No.: US 11,117,165 B2
(45) Date of Patent: Sep. 14, 2021

(54) CAPACITIVE MICROMACHINED ULTRASONIC TRANSDUCERS WITH OVERCURRENT PROTECTION

(71) Applicant: KONINKLIJKE PHILIPS N.V., Eindhoven (NL)

(72) Inventors: Bernard Joseph Savord, Andover, MA (US); Richard Edward Davidsen, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 668 days.

(21) Appl. No.: 15/751,252

(22) PCT Filed: Aug. 2, 2016

(86) PCT No.: PCT/IB2016/054628
§ 371 (c)(1),
(2) Date: Feb. 8, 2018

(87) PCT Pub. No.: WO2017/025856
PCT Pub. Date: Feb. 16, 2017

(65) Prior Publication Data
US 2018/0229269 A1    Aug. 16, 2018

Related U.S. Application Data

(60) Provisional application No. 62/203,536, filed on Aug. 11, 2015.

(51) Int. Cl.
*B06B 1/02* (2006.01)
*A61B 8/00* (2006.01)
(Continued)

(52) U.S. Cl.
CPC .......... *B06B 1/0292* (2013.01); *A61B 8/4483* (2013.01); *A61B 8/488* (2013.01); *G01S 7/5208* (2013.01); *G01S 7/52026* (2013.01); *G01S 15/895* (2013.01); *A61B 8/14* (2013.01); *B06B 2201/51* (2013.01); *B06B 2201/76* (2013.01);
(Continued)

(58) Field of Classification Search
None
See application file for complete search history.

(56) References Cited

U.S. PATENT DOCUMENTS 5,997,479 A    12/1999  Savord et al.
6,013,032 A     1/2000  Savord
(Continued)

FOREIGN PATENT DOCUMENTS

JP    2011166632 A    8/2011

*Primary Examiner* — Yi-Shan Yang

(57) ABSTRACT

An array of CMUT cells has a DC bias voltage coupled to the top electrodes of the cells to bias the electrode to a desired collapsed or partially collapsed state. In the event of a short-circuit failure of a CMUT cell a protection circuit for the cell senses an over-current condition and responds by opening the DC current path through the failed cell. The protection circuit further disables the transmit and receive circuitry of the cell. In another implementation a sense circuit senses an over-current condition of the DC bias supply and responds by disabling all of the CMUT cells of the array, then sequentially re-enabling them, except that an attempt to re-enable a failed cell results in that cell remaining in a disabled state.

18 Claims, 5 Drawing Sheets

(51) Int. Cl.
  *G01S 7/52*    (2006.01)
  *A61B 8/08*    (2006.01)
  *G01S 15/89*   (2006.01)
  A61B 8/14      (2006.01)
  G01N 29/24     (2006.01)
(52) U.S. Cl.
  CPC ...... *G01N 29/2406* (2013.01); *G01S 15/8925* (2013.01)

(56) References Cited

U.S. PATENT DOCUMENTS

| | | |
|---|---|---|
| 6,283,919 B1 | 9/2001 | Roundhill et al. |
| 6,328,697 B1 | 12/2001 | Fraser |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 7,293,462 B2 | 11/2007 | Lee et al. |
| 7,549,962 B2 | 6/2009 | Dreschel et al. |
| 7,589,455 B2 | 9/2009 | Adachi et al. |
| 8,431,420 B2 | 4/2013 | Kobayashi et al. |
| 9,132,693 B2 | 9/2015 | Klootwijk |
| 2006/0145059 A1* | 7/2006 | Lee ............... H04R 23/00 250/214 R |
| 2012/0008238 A1* | 1/2012 | Thiele ............ H02H 7/0838 361/18 |
| 2012/0069715 A1* | 3/2012 | Okuno ............ B06B 1/0292 367/180 |
| 2013/0064035 A1* | 3/2013 | Kandori .......... B06B 1/0207 367/7 |
| 2014/0184383 A1 | 7/2014 | Wodnicki |

* cited by examiner

CAPACITIVE MICROMACHINED ULTRASONIC TRANSDUCERS WITH OVERCURRENT PROTECTION

This application is the U.S. National Phase application under 35 U.S.C. § 371 of International Application No. PCT/IB2016/054628, filed on Aug. 2, 2016, which claims the benefit of Provisional Application Ser. No. 62/203,536 filed Aug. 11, 2015. These applications are hereby incorporated by reference herein.

FIELD OF THE INVENTION

This invention relates to medical diagnostic ultrasonic imaging and, in particular, to ultrasonic transducer probes which use capacitive micromachined ultrasonic transducers (CMUTs).

BACKGROUND OF THE INVENTION

Traditionally, ultrasonic transducers are formed of piezoelectric ceramic materials such as PZT or of piezoelectric polymers such as PVDF. Recently it has been shown that transducers can be made by semiconductor processes. Such transducers are formed of tiny semiconductor cells in which a vibrating membrane generates and receives the ultrasonic energy and are referred to as micromachined ultrasonic transducers (MUTs.) Two such transducer types are those which utilize a piezoelectric material on the membrane called piezoelectric micromachined ultrasonic transducers (PMUTs) and those which utilize a capacitive effect between a conductive membrane and another electrode called capacitive micromachined ultrasonic transducers (CMUTs.) Individual transducer elements may be formed of dozens or hundreds of such MUT cells operating in unison. Since these cells are very small, each MUT cell only produces or responds to a small amount of acoustic energy. Two approaches are commonly used to increase the acoustic efficiency of MUT devices. One is to bias the cells with a DC bias voltage which, in the case of CMUTs, brings the vibrating membrane into close proximity to the opposing electrode, increasing the sensitivity of the devices. Another is to form an array of cells which are very close to each other, maximizing the density of the cells on their substrate and providing a large number of cells which are operated in unison as a single transducer element. The high density fabrication of the cells also improves their grating lobe characteristics and reduces clutter in the resultant ultrasonic images.

A transducer array or even an individual element can thus comprise hundreds or thousands of individual MUT cells which are biased by the DC bias voltage. While such an architecture has numerous performance advantages as described above, a problem arises in that the failure of a single MUT cell can render a vast number of cells inoperative. It is possible for a single cell to fail by collapse of the membrane with its high DC bias voltage onto the opposing electrode. This shorts out not only the failed cell, but also all of the hundreds or thousands of other cells with which it is commonly biased. While the failure of a single cell by itself may not appreciably affect the performance of the transducer probe, the shorting out of a large number of other cells can render the entire transducer probe inoperative. One approach to prevent this problem is described in U.S. Pat. No. 7,293,462 (Lee et al.) The approach of Lee et al. is to form a fuse at the end of a row or column of interconnected MUT cells which will open when one cell in the row or column shorts out. This will remove the row or column of cells from operation in the transducer, allowing the other cells in the transducer to remain functioning. There are several drawbacks to this approach, however. One is that each row or column of interconnected cells must be separately biased, increasing the complexity of providing bias voltages to all of the cells in the probe. Another is that a fuse occupies a relatively large area on the MUT substrate, decreasing the area on the substrate available for MUT cells and hence the sensitivity of the transducers. Yet another is that a plurality of cells are removed from operation in the probe, the failed cell as well as the others to which it is connected, which also degrades the performance of the ultrasound probe. It would be desirable to be able to remove only a failed cell from operation, allowing the other fully functioning cells to remain in operation.

Accordingly it is an objective of the present invention to increase the lifetime of a MUT probe by removing only a failed MUT cell from operation, allowing the remaining fully functional cells to remain in operation. It is a further objective to do so in a way which does not utilize substrate area that could otherwise be used for MUT fabrication, thereby maintaining the MUT density of the MUT array and hence its sensitivity.

SUMMARY OF THE INVENTION

In accordance with the principles of the present invention, an ultrasonic transducer MUT cell array with a plurality of CMUT cells, wherein each MUT cell has a membrane comprising a top electrode and a bottom electrode coupled to the substrate, wherein one of the top or bottom electrodes is a common electrode arranged to be coupled to a common reference potential (reference voltage), while another electrode is a signal electrode arranged to be coupled to an a.c. signal. The MUT array further has a protection circuit coupled to one of the electrodes of an individual cell of the array, said circuit is adapted to open (interrupt) a cell's current path and to isolate only a failed cell from the remaining cells in the array, which remain fully operational. An exemplary protection circuit operates in the manner of a circuit breaker to open the cell's current path in the event of an over-current condition.

In one of the embodiments, the protection circuit is coupled to the signal electrode. The advantage of this solution is that placing the circuit on the signal side by coupling it to the a.c. signal bearing electrode allows a quick and efficient deactivation of the failed cell by keeping the density of the MUT array maximized. In further development of this embodiment the protection circuit further may comprise transmit circuitry and receive circuitry coupled to the current path. In this way a further minimization of the array whilst keeping the same sensitivity (via array cell density) can be achieved.

In another embodiment, common electrodes of the MUT cells are interconnected and coupled to the same reference potential. This simplifies designs of the array.

In another embodiment the ultrasonic transducer MUT cell array can comprise a DC bias voltage supply arranged to provide a bias potential (either a common potential with respect to the common electrode or a D.C. reference potential with respect to the signal electrode). In the preferred embodiment, the DC bias supply coupled to an electrode of each of the plurality of MUT cells to bias the cell electrodes to a partially or fully collapsed state. In one example only a single fault sensing circuit is needed for the DC bias supply. The protection circuits act to disable all the MUT cells of the array initially, then re-enables them one by one until all operational cells are re-enabled and only the failed cell is disabled. In a preferred implementation the protection circuits are formed on an application-specific integrated circuit (ASIC) which controls the individual MUTs. By forming the protection circuits on a high density ASIC, no area of the MUT substrate which could otherwise be used for MUT fabrication is used for the protection circuits, maintaining a high cell density on the MUT substrate for good acoustic performance. The control ASIC may be formed as a separate integrated circuit chip such as one used for microbeamforming which is bonded to the MUT substrate by known techniques, or the ASIC may be formed on the substrate used for MUT fabrication.

DETAILED DESCRIPTION OF THE EMBODIMENTS

Figure 1:
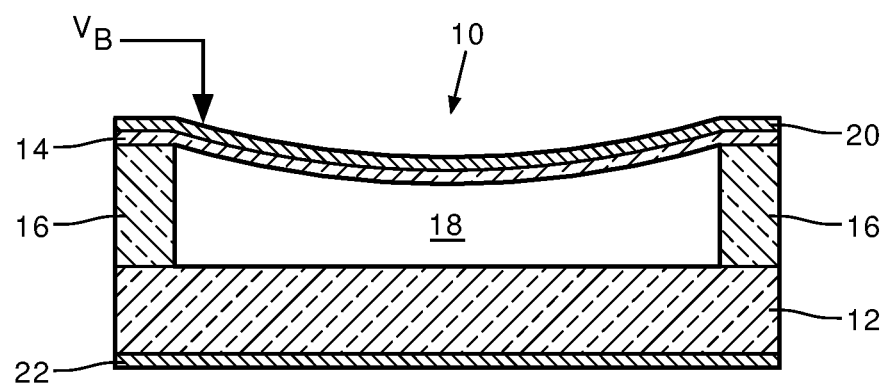
FIG. 1 is a cross-sectional view of a typical suspended membrane CMUT transducer cell.

CMUTs were initially constructed to operate in what is now known as a suspended or "uncollapsed" mode. Referring to FIG. 1, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied across the electrodes 20,22 will modulate the capacitance, causing the membrane to move and thereby transmit an acoustic signal. A DC bias voltage $V_B$ is also applied across the electrodes, drawing the membrane and its top electrode 20 into close proximity with the floor of the cavity of the cell to increase sensitivity.

Figure 2:
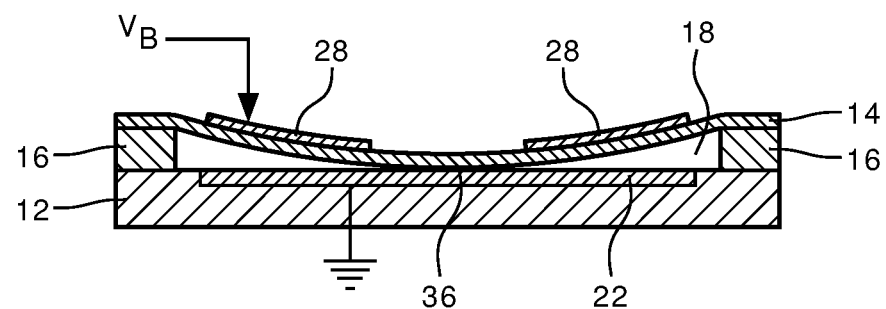
FIG. 2 is a cross-sectional view of a CMUT cell being operated in the collapsed mode.

FIG. 2 is a schematic cross-section of a CMUT cell which is operated in the collapsed mode. The CMUT cell includes a substrate layer 12 such as silicon, a substrate electrode 22, a membrane layer 14, and a membrane electrode ring 28. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. The cell and its cavity 18 may define alternative geometries. For example, cavity 18 could define a rectangular and/or square cross-section, a hexagonal cross-section, an elliptical cross-section, or an irregular cross-section.

The bottom electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduced charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with collapsed mode CMUT, which are more susceptible to charge retention than are uncollapsed device. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 2, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

In FIG. 2 the CMUT cell membrane layer is biased to a collapsed state, in which the membrane 14 is in contact with the floor of the cavity 18. This is accomplished by applying a DC bias voltage (supplied by the D.C. bias supply) to the two electrodes as indicated by voltage $V_B$ applied to the electrode ring 28 and a reference potential (ground) applied to the substrate electrode 22. In a preferred implementation of a CMUT cell of the present invention, the bottom electrode has a function of a signal bearing electrode, it is not grounded but coupled to a DC reference potential and the a.c. drive signal for the cell (as well as received signals) are applied to and received at the bottom electrode. While the electrode ring 28 could also be formed as a continuous disk without the hole in the center, FIG. 2 illustrates why this is not necessary. When the membrane 14 is biased to its precollapsed state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

Figure 3:
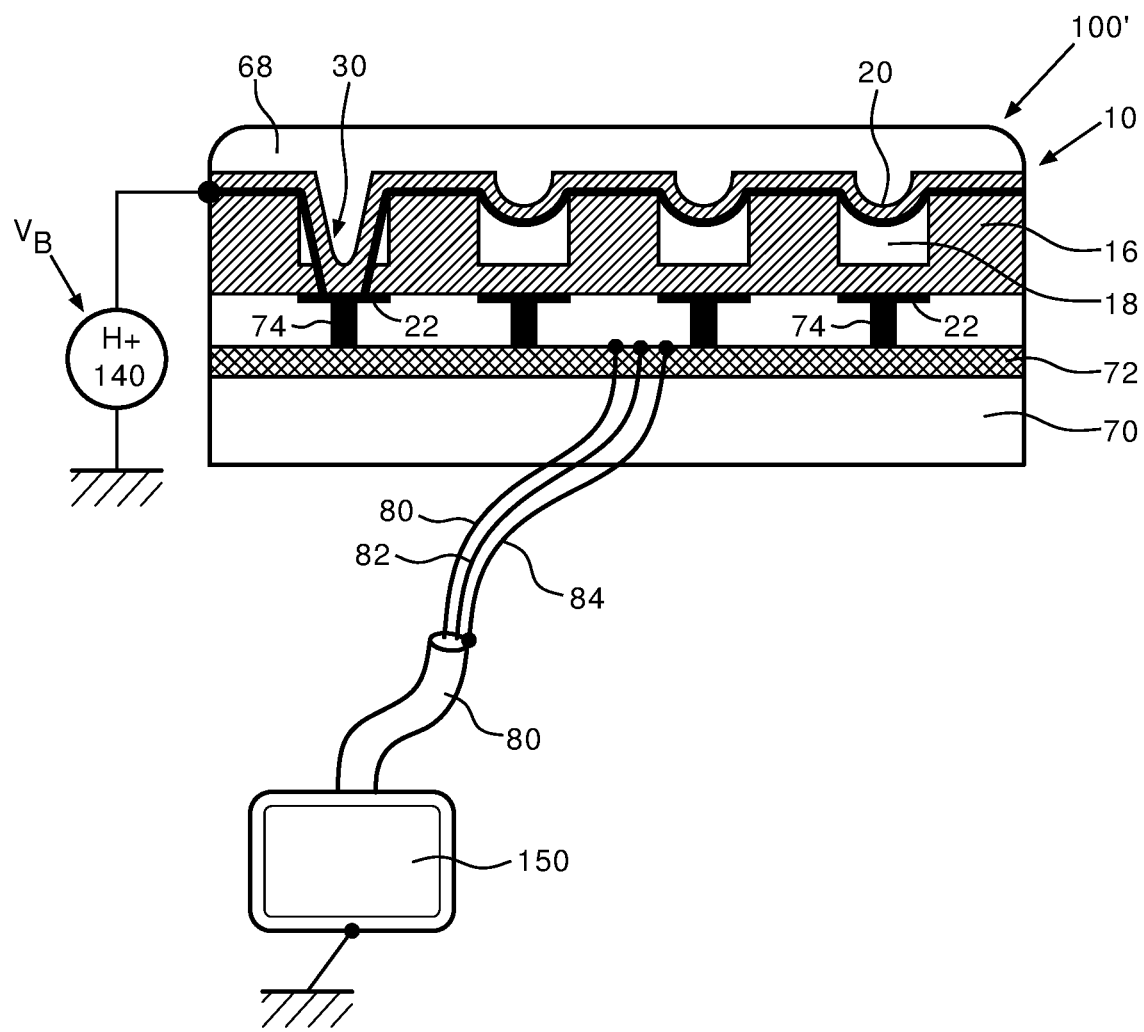
FIG. 3 is a cross-sectional view of an array of commonly biased CMUT cells illustrating the failure mode when one of the cells shorts out.

FIG. 3 illustrates a CMUT transducer probe 100' connected to an ultrasound system represented at 150 in the drawing. Shown in this illustration is an array of four CMUT cells 10 with a common top electrode 20 and individual bottom electrodes 22 for each CMUT cell. Dielectric 16 supports the top electrodes and membranes across the cavity 18 of each cell which allows the membranes and top electrodes to move in response to an applied DC bias voltage $V_B$ and received ultrasonic energy. A DC bias voltage H+ ($V_B$) provided by a DC bias supply 140 is applied to the common electrode 20 to bias the top electrodes in the desired proximity with the floors of the cavities 18. In a non-limiting example of FIG. 3 the top (common) electrodes 20 of the CMUT cells are shown to be interconnected, therefore forming a continues electrode with the common voltage potential (either ground or reference bias). A lens 68 or other covering protects the patient from direct contact with the high voltage of the DC bias. In accordance with a preferred implementation the CMUT cells are fabricated on a substrate 70 of an ASIC of control integrated circuitry 72 for the CMUT cells. Alternatively, the bottom electrode 22 of each cell is the signal bearing electrode, while the top electrode 20 (common electrode) of each cell can be grounded (coupled to the ground potential). Therefore, further improving patient safety of the array. The signal electrodes 22 of the CMUT cells are electrically connected to the circuitry of the ASIC by vias 74 through the top surface of the ASIC. Alternatively the CMUT can be formed on its own substrate 12 and connected to a separate ASIC through any of a number of techniques known to those skilled in the art such as flip chip connection, conductive adhesives, or through silicon vias. The ASIC circuitry of the ultrasound probe is connected to the ultrasound system 150 by a cable 80. The ultrasound system controls the transducer electronics of the ASIC through analog or digital control lines 82 and receives ultrasound signals through analog or digital signal lines 84.

FIG. 3 illustrates the problem addressed by the present invention, which is that the left-most CMUT cell has failed and its suspended top electrode 20 has collapsed to its bottom electrode 22 as shown at 30, shorting out the CMUT cell (causing an over-current condition). Since the top electrodes of the cells are common (share common potential), this failure also shorts out the top electrodes of all of the other interconnected cells. Not only are the cells now inoperative, but the coupling of the DC bias voltage directly to the via 74 applies current from the DC bias supply directly to the ASIC 72, potentially damaging the integrated circuitry of the ASIC.

Figure 4:
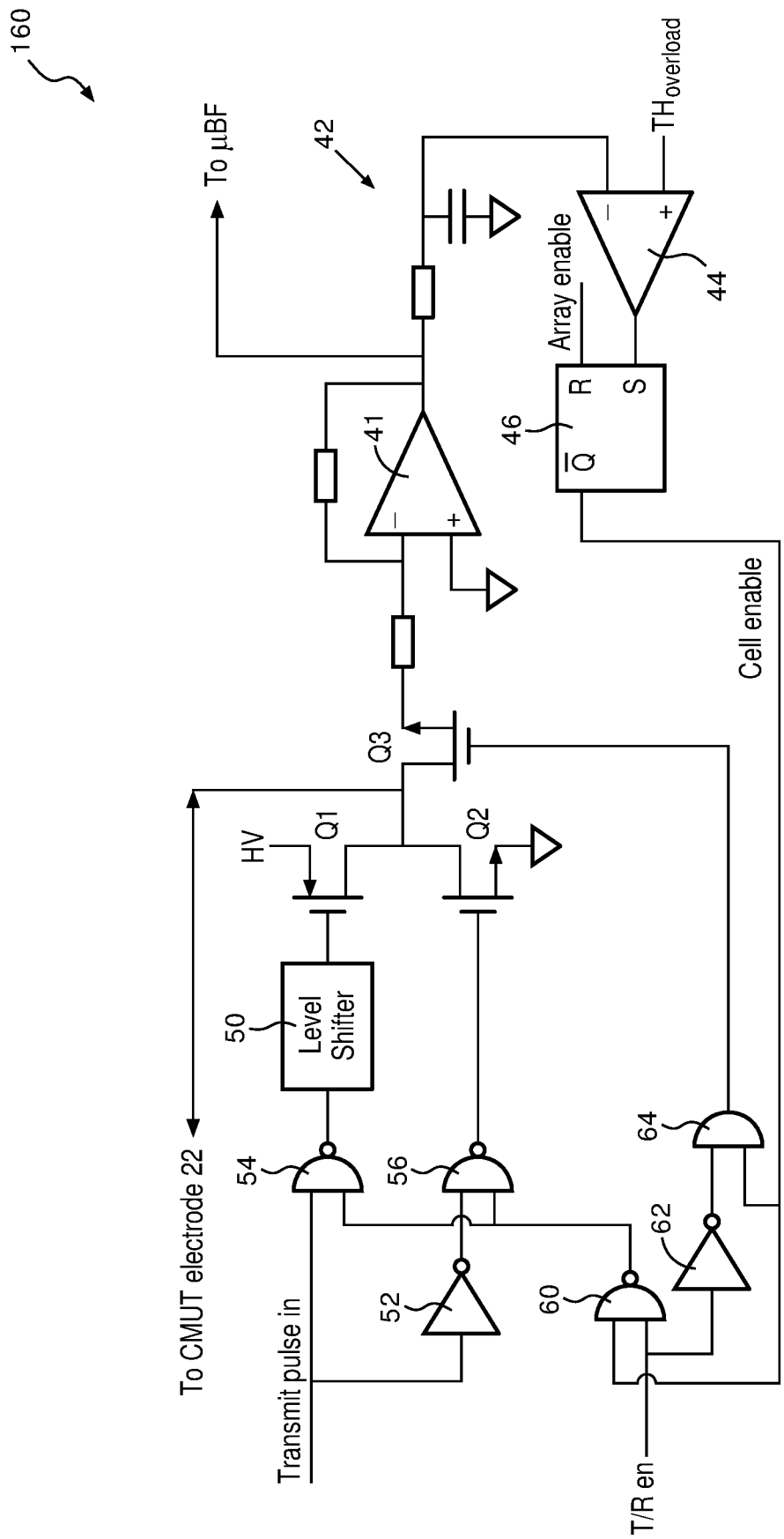
FIG. 4 is a schematic diagram of a first protection circuit constructed in accordance with the principles of the present invention.

FIG. 4 illustrates a first protection circuit 160 for a CMUT cell failure constructed in accordance with the principles of the present invention. The protection circuits described herein can be fabricated on any substrate of the probe, but preferably are fabricated as part of ASIC 72 on its substrate. A CMUT cell or group of cells (if it is desired to protect a group of cells with one protection circuit) is tied to the drain electrodes of transistors Q1, Q2 and Q3. In general, one of the CMUT electrodes (in this embodiment the signal electrode 22) can be coupled to a sense circuit arranged to sense the over-current condition through the electrode and to initiate the interruption of the current path. The breakdown voltage of these transistors is chosen to handle the bias voltage that would appear when a short of the CMUT electrodes occurs. In a preferred implementation the transistors are fabricated as integrated circuit elements on the same substrate as the ASIC cireuitry, using a semiconductor process rating at least equal to the high bias voltage of the DC bias supply. Alternatively, the DC bias voltage can be chosen to be within the operating voltage range of the integrated circuit transistors, when possible. Transistors Q1 and Q2 are transmit circuitry for the CMUT cell and operate to cause the CMUT to transmit an acoustic wave or pulse, and transistor Q3 is receive circuitry which operates during reception of echo signals. These transistors act as current limiters to avoid excess damage to other operating cells of a CMUT array as well as their control circuitry when a short occurs. Q1 and Q2 form high voltage pulsers for generating acoustic transmit events. These transistors are controlled by the "transmit_pulse_in" signal when a "transmit and receive enable" (T/R en) signal is high, and are disabled by setting the T/R en signal low during the receive mode or by setting an SR flip flop 46 to produce a low "cell enable" signal as described below. When the CMUT is to produce a transmit pulse or wave, a high T/R en signal and a high cell enable signal together cause gate 60 to enable gates 54 and 56. A low output signal from gate 54 is coupled to the gate of transistor Q1, causing it to apply a transmit pulse to CMUT electrode 22. Since Q1 is a high voltage transistor for transmit, it is isolated from low voltage NAND gate 54 by a level shifter 50. The level shifter may be constructed as shown in U.S. patent application of one of us, entitled "CAPACITIVE MICROMACHINED ULTRASONIC TRANSDUCERS WITH INCREASED PATIENT SAFETY", U.S. Ser. No. 15/750,604. As shown therein a level shifter comprises an input buffer biased to the voltage of its input circuit and an output buffer biased to the voltage of its output circuit, separated by an a.c. coupling element such as a capacitor, a transistor, a transformer, or a photo diode. At the conclusion of the transmit pulse Q1 is switched off in response to the end of the transmit pulse in signal and Q2 is turned on to terminate the transmit interval. Transistor Q3 acts as a transmit/receive switch that couples the bottom electrode 22 of the protected CMUT to a preamplifier 40 in receive mode. This occurs when the T/R en signal goes low, causing the output of gate 64 to go high in conjunction with the high cell enable signal. Received ultrasound signals are thereby amplified and coupled to a microbeamformer or other ultrasound signal processor for further processing.

Transistors Q1, Q2 and Q3 are all disabled (nonconductive) when the SR flip flop 46 is set, causing the cell enable signal to go low and gates 60 and 64 to produce low output signals. In this condition damaging current flow through the failed CMUT cell is prevented, preventing the circuitry from subsequent damage. In the event of an over-current condition of a failed CMUT cell, the excessive current is momentarily coupled by preamplifier 40 to an input of a sense comparator 44. The comparator 44 senses the over-current condition by comparing the resulting voltage at one input with an overload threshold voltage $Th_{overload}$ at the other input. When the applied voltage exceeds the overload threshold, comparator 44 switches its output and sets RS flip-flop 46. The setting of flip-flop 46 causes the cell enable signal produced at its Q-not output to go low, disabling transistors Q1, Q2, and Q3 and protecting the CMUT cell and its circuitry.

An RC filter 42 is coupled between preamplifier 40 and the input to the comparator 44 to prevent normal transient high voltage ultrasound signals from affecting the comparator and causing it to switch unnecessarily. When the CMUT probe is first powered on, an "array enable" signal is applied to the reset input of the RS flip-flop 46 of every protection circuit of the CMUT array, thereby initially setting all of the cell enable signals of the array high for intended normal operation. If a cell failure is present at power-on, the resultant quiescent offset at the output of preamplifier 40 is detected by comparator 44, setting flip-flop 46 to the disable condition to protect the CMUT cell and its circuitry. The protection circuit of FIG. 4 is designed for use with every CMUT cell of an array.

Figure 5:
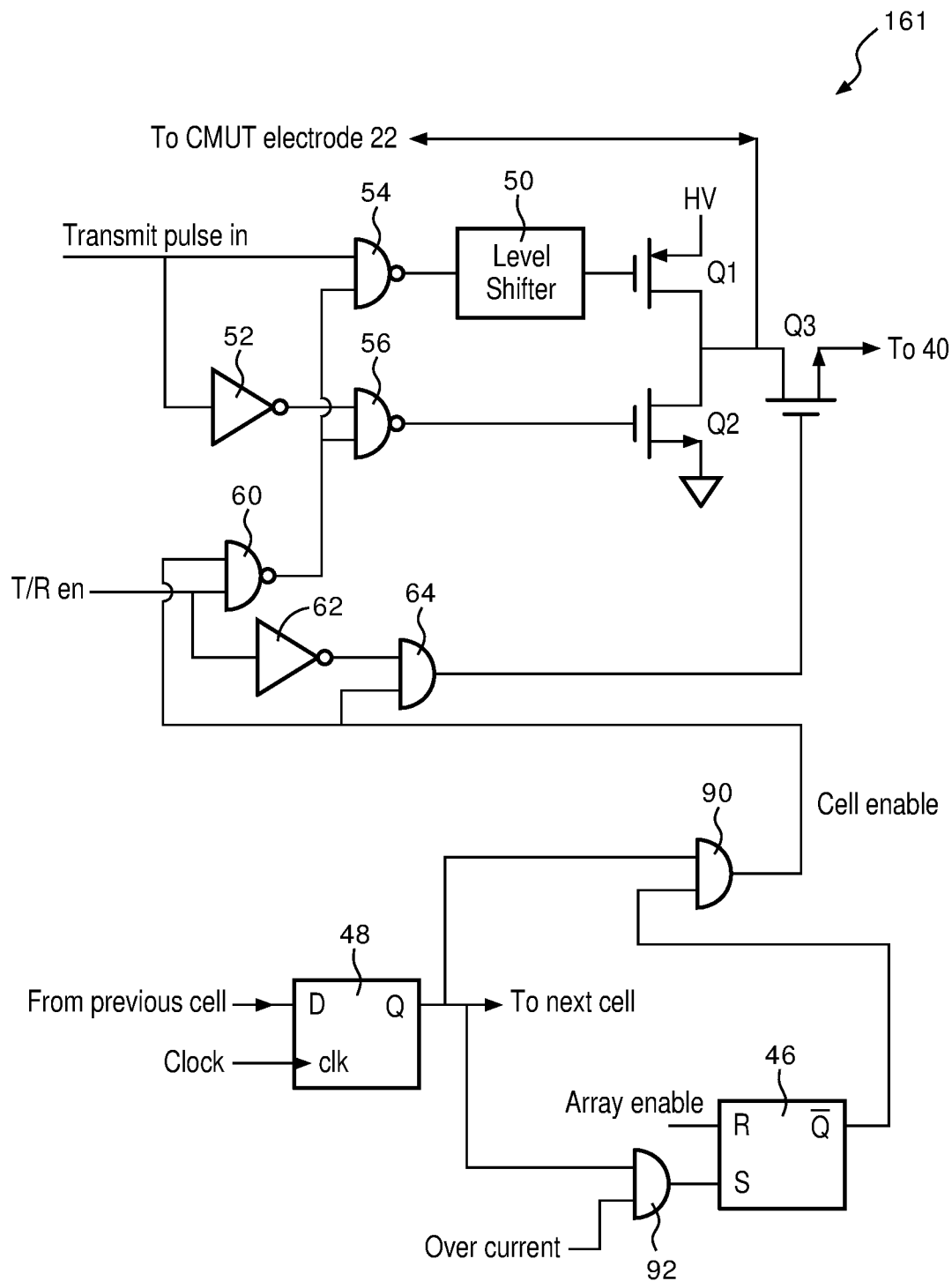
FIG. 5 is a schematic diagram of a second protection circuit constructed in accordance with the principles of the present invention.
Figure 6:
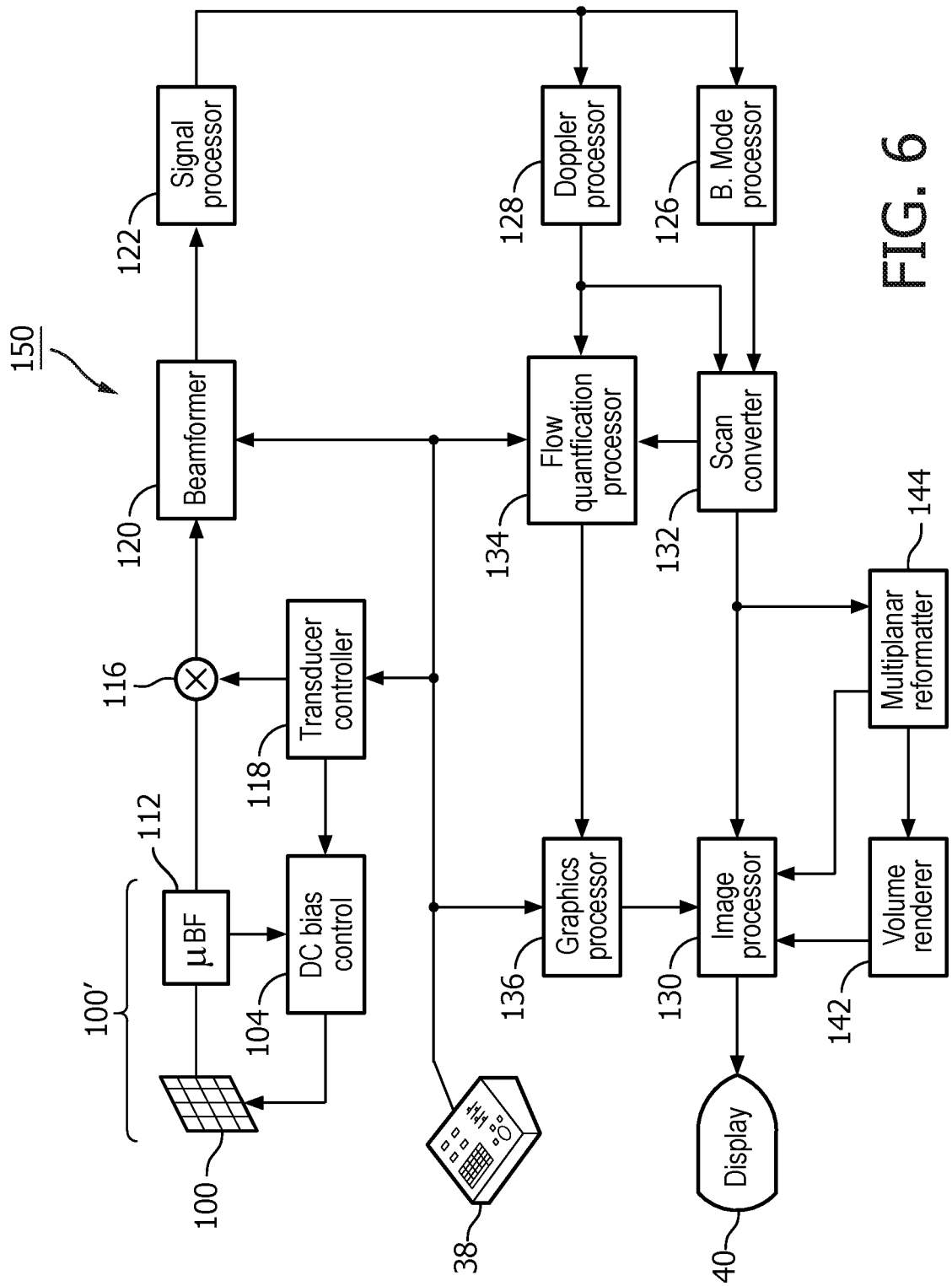
FIG. 6 is a block diagram of an ultrasonic imaging system suitable for use with a circuit breaker protected CMUT cell array of the present invention.

FIG. 5 illustrates a second protection circuit for a CMUT cell failure 161 constructed in accordance with the principles of the present invention. This second protection circuit requires only a single over-current sense circuit coupled to sense the current of the DC bias circuit $V_B$. In the event of a short of one of the CMUT cells connected to the DC bias circuit, all of the CMUT cells are immediately disabled, then sequentially re-enabled except for the cell which has the fault. The over-current sense circuit can be constructed in the same manner as a conventional sensing circuit for such conditions. For example, a comparator such as comparator 44 can have one input coupled to an over-current reference voltage against which the operation of the DC bias circuit is compared. The other input is coupled to receive a voltage which varies directly with changes in the current produced by the DC bias supply, such as by use of a sense resistor coupled to the supply. When the sensed current of the DC bias supply exceeds (or falls below) the reference voltage, an over-current condition is sensed and the comparator produces an over-current indication signal.

The components in the upper portion of FIG. 5 are the same as those with the same reference numbers in FIG. 4 and will not be described again. In the implementation of FIG. 5 the cell enable signal is produced by a gate 90, which receives inputs from the RS flip-flop 46 and a D-type flip-flop 48. The flip-flop 48 is coupled in a chain with the other D-type flip-flops 48 of the other protection circuits for the other cells, forming which is effectively a shift register. When the flip-flop of one protection circuit is set during one clock cycle, its high Q output is applied to the D input of the next protection circuit, which enables the flip-flop of the next protection circuit to be set during the next clock cycle. This causes the circuits for all of the cells in the array to be tested for an over-current condition one at a time.

When the CMUT probe is powered on, the RS flip-flops 46 of all of the protection circuits are, as before, reset by an array enable signal to enable all of the CMUT cells. This applies a high signal to one input of gate 90. The shift register of D-type flip-flops is clocked to sequentially set all of the flip-flops to a high Q output, and this high signal is applied to the other input of gate 90, the concurrence causing gate 90 to produce a high "cell enable" signal which allows normal operation of each CMUT cell of the array. In the event that an over-current condition is sensed at the DC bias supply, which would occur in the event of a short-circuit of a cell, all of the RS flip-flops and all of the flip-flops 48 of the shift register are reset, and the low Q output of flip-flop 48 produces a disabling cell enable signal at the output of gate 90 of every protection circuit for every CMUT cell of the array. With the current path of every CMUT cell thus disabled, the over-current condition through the failed cell is thus momentarily ended. Now the CMUT cells are re-enabled, one at a time. The shift register of D-type flip-flops is clocked, setting the first flip-flop 48 in the sequence. The flip-flop 48 produces a high Q output which, together with the high signal from RS flip-flop 46, causes gate 90 to produce a cell enable signal, re-enabling one of the CMUT cells. If that cell is operating normally, its protection circuit remains in this state and the high output signal at the Q output of its flip-flop 48 is used to set the next D-type flip-flop in the chain at the next clock cycle. This activates the next CMUT cell and, if again the cell is operating normally, this sequence of cell testing continues.

If one of the CMUT cells has short-circuited, eventually the flip-flop 48 for that failed cell's protection circuit will be set, which will cause the cell to be enabled and transistor Q2 or Q3 of its receive circuit to be rendered conductive. This will cause high current to be drawn through the failed cell and the DC bias supply to again experience the over-current condition. The over-current sense circuit of the supply (e.g., its comparator) then produces a high over-current indication signal which is applied to one input of a gate 92 which, together with the high output signal from flip-flop 48, cause gate 92 to set the RS flip-flop 46 of the protection circuit, thereby disabling transistors Q1, Q2, and Q3 of the protection circuit of this CMUT. The shift register operation will continue, re-enabling the other operational CMUT cells of the array until all of the CMUT cells have been re-enabled for normal operation except for the one that short-circuited.

FIG. 7 illustrates in block diagram form an ultrasonic diagnostic imaging system 150 suitable for use with a MUT array probe of the present invention. A CMUT array 100 is located on the tip of a catheter or distal end of an ultrasound probe 100', together with a microbeamformer ASIC 112. The CMUT array 100 can be a one- or a two-dimensional array of MUT transducer elements capable of scanning in a 2D plane or in three dimensions for 3D imaging. The microbeamformer ASIC 112 controls the transmission and reception of signals by the CMUT array cells and also houses the protection circuits for the CMUT cells as described above. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled to transmit/receive (T/R) switches 116 which switch between transmission and reception and protect the main system beamformer 120 from high energy transmit signals when a microbeamformer is not used and a transducer array is operated directly by the main system beamformer. The transmission of ultrasonic beams from the CMUT transducer array 100 under control of the microbeamformer ASIC 112 is directed by a transducer controller 118 coupled to the T/R switch and the main system beamformer 120, which receives input from the user's operation of the user interface or control panel 38. One of the functions controlled by the transducer controller is the direction in which beams are steered. Beams may be steered straight ahead from (orthogonal to) the transducer array, or at different angles for a wider field of view. The transducer controller 118 also controls a circuit 104 for the DC bias applied to the CMUT cells which biases the cell membranes 14 to a partially or fully collapsed state for operation of the CMUTs in the desired mode of operation.

The partially beamformed signals produced by the microbeamformer 112 on receive are coupled to a main beamformer 120 where partially beamformed signals from individual patches of transducer elements are combined into a fully beamformed signal. For example, the main beamformer 120 may have 128 channels, each of which receives a partially beamformed signal from a patch of dozens or hundreds of CMUT transducer cells.

In this way the signals received by thousands of transducer elements of a CMUT transducer array can contribute efficiently to a single beamformed signal. In a basic implementation the acoustic signals received from rows of CMUT cells are processed into beams from an image plane in front of the rows of cells to form a scanned 2D image.

The beamformed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 126 and a Doppler processor 128. The B mode processor 126 employs amplitude detection for the imaging of structures in the body such as the tissue of organs and vessels in the body. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 128 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 132 and a multiplanar reformatter 144. The scan converter arranges the echo signals in the spatial relationship from which they were received into a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 142 to an image processor 130 for further enhancement, buffering and temporary storage for display on an image display 40. In addition to being used for imaging, the blood flow velocity values produced by the Doppler processor 128 are coupled to a flow quantification processor 134. The flow quantification processor produces measure of different flow conditions such as the volume rate of blood flow. The flow quantification processor may receive input from the user control panel 38, such as the point in the anatomy of an image where a measurement is to be made. Output data from the flow quantification processor is coupled to a graphics processor 136 for the reproduction of measurement values with the image on the display 40. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transducer controller 118 to control the generation of ultrasound signals from the transducer array 100 and hence the images produced by the transducer array and the ultrasound system. The user interface is also coupled to the multiplanar reformatter 144 for selection and control of a display of multiple multiplanar reformatted (MPR) images which may be used to perform quantified measures in the image field of the MPR images.

The invention claimed is:

1. A micromachined ultrasonic transducer (MUT) array arranged to be protected from an over-current condition comprising:
   a substrate;
   a plurality of MUT cells formed on the substrate, each MUT cell of the plurality of MUT cells having a membrane comprising a top electrode and a bottom electrode coupled to the substrate,
      wherein one of the top electrode or the bottom electrode is a common electrode arranged to be provided with a common reference potential and the other of the top electrode or the bottom electrode is a signal electrode arranged to be coupled to an alternating current (AC) signal; and
   a protection circuit comprising a sense circuit, and being coupled to a current path of one of the top electrode or the bottom electrode of each MUT cell,
      wherein the sense circuit is coupled to the current path and adapted to sense the over-current condition, and
      wherein the protection circuit is arranged to interrupt the current paths to disable the plurality of MUT cells and to re-enable only operational MUT cells of the plurality of MUT cells such that a failed MUT cell is isolated from the operational MUT cells under the over-current condition.

2. The micromachined ultrasonic transducer (MUT) array of claim 1, wherein the signal electrode is the bottom electrode and the protection circuit is further coupled to said bottom electrode of the MUT cell.

3. The micromachined ultrasonic transducer (MUT) array of claim 2, wherein the protection circuit further comprises transmit circuitry and receive circuitry coupled to the current path, wherein the transmit circuitry and the receive circuitry are arranged to provide the AC signal.

4. The micromachined ultrasonic transducer (MUT) array of claim 3, wherein the protection circuit is further arranged to disable the receive circuitry in the event of the over-current condition.

5. The micromachined ultrasonic transducer (MUT) array of claim 4, wherein the protection circuit is further arranged to disable the transmit circuitry in the event of the over-current condition.

6. The micromachined ultrasonic transducer (MUT) array of claim 5, wherein the sense circuit further comprises a comparator arranged to compare a signal of the current path with a reference signal.

7. The micromachined ultrasonic transducer (MUT) array of claim 6, wherein the comparator is adapted to produce an output signal that disables the transmit circuitry and the receive circuitry of the protection circuit in the event of the over-current condition.

8. The micromachined ultrasonic transducer (MUT) array of claim 1, wherein the protection circuits are further arranged to sequentially re-enable the operational MUT cells.

9. The micromachined ultrasonic transducer (MUT) array of claim 8, wherein the protection circuits are further arranged to sequentially re-enable the operational MUT cells by means of a shift register.

10. The micromachined ultrasonic transducer (MUT) array of claim 1, wherein an attempt by the protection circuit to re-enable the failed MUT cell results in the failed MUT cell remaining disabled.

11. The micromachined ultrasonic transducer (MUT) array of claim 1, wherein the protection circuit is located on the same substrate as the plurality of MUT cells.

12. The micromachined ultrasonic transducer (MUT) array of claim 1, wherein the protection circuit is located on a different substrate from that of the plurality of MUT cells.

13. The micromachined ultrasonic transducer (MUT) array of claim 1 further comprising a direct current (DC) bias voltage supply coupled to the common electrode and arranged to provide the common reference potential to said common electrode,
wherein the common reference potential corresponds to a voltage V, wherein at least a portion of the protection circuit is coupled to the current path, and wherein the portion of the protection circuit exhibits a breakdown voltage which is at least equal to V.

14. The micromachined ultrasonic transducer (MUT) array of claim 13, wherein the portion of the protection circuit further comprises integrated receive circuitry for the plurality of MUT cells.

15. The micromachined ultrasonic transducer (MUT) array of claim 14, wherein the portion of the protection circuit further comprises a current limiter.

16. The micromachined ultrasonic transducer (MUT) array of claim 13, wherein the portion of the protection circuit further comprises integrated transmit circuitry for the plurality of MUT cells.

17. The micromachined ultrasonic transducer (MUT) array of claim 16, wherein the portion of the protection circuit further comprises a current limiter.

18. The micromachined ultrasonic transducer (MUT) array of claim 1 further comprising a direct current (DC) bias voltage supply coupled to the common electrode and arranged to provide the common reference potential to said electrode,
wherein at least a portion of the protection circuit is coupled to the current path, wherein the portion of the protection circuit further comprises integrated circuitry fabricated with a process rating of voltage V, and wherein the common reference potential corresponds to a bias voltage that does not exceed voltage V.

* * * * *